US012582659B2

(12) United States Patent
Khouider et al.

(10) Patent No.: US 12,582,659 B2
(45) Date of Patent: *Mar. 24, 2026

(54) STIMULANT COMPOSITION AND PROCESS FOR MAKING SAME

(71) Applicant: ALL LABS, INC., Dover, DE (US)

(72) Inventors: Mohand Khouider, Austin, TX (US); Chaim Weinerman, Jamaica Plain, MA (US)

(73) Assignee: ALL LABS, INC., Dover, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/323,694

(22) Filed: Sep. 9, 2025

(65) Prior Publication Data

US 2026/0007677 A1 Jan. 8, 2026

Related U.S. Application Data

(63) Continuation of application No. 17/618,557, filed as application No. PCT/CA2020/050529 on Apr. 22, 2020, now Pat. No. 12,433,894.

(Continued)

(51) Int. Cl.

*A61K 31/522* (2006.01)
*A23L 2/56* (2006.01)

(Continued)

(52) U.S. Cl.

CPC .............. *A61K 31/522* (2013.01); *A23L 2/56* (2013.01); *A23L 2/60* (2013.01); *A23L 33/105* (2016.08); *A23L 33/175* (2016.08); *A61K 9/0053* (2013.01); *A61K 9/08* (2013.01); *A61K 31/198* (2013.01); *A61K 36/41* (2013.01); *A23V 2002/00* (2013.01)

(58) Field of Classification Search

CPC ............................ A61K 31/522; A23L 33/175
USPC .......................................................... 514/567
See application file for complete search history.

(56) References Cited

U.S. PATENT DOCUMENTS 5,456,677 A 10/1995 Spector
8,993,033 B2 3/2015 Bhargava (Continued)

FOREIGN PATENT DOCUMENTS

CA 2959004 A1 8/2018
KR 20130109282 A 10/2013

(Continued)

OTHER PUBLICATIONS

Caffeine+N-Acetyl Tyrosine Solution, Natrium Health, 1-3. (Year: 2019).*

(Continued)

*Primary Examiner* — Jeffrey S Lundgren
*Assistant Examiner* — Heather Dahlin
(74) *Attorney, Agent, or Firm* — Mintz, Levin, Cohn, Ferris, Glovsky and Popeo, P.C.

(57) ABSTRACT

A liquid composition for use as a consumable stimulant; it has a consumable liquid solvent comprising water; caffeine at a concentration of at least 0.04 g/mL once dissolved in the consumable liquid solvent; and a tyrosine-based compound, wherein the presence of the tyrosine-based compound results in an increased solubility of the caffeine in the consumable liquid solvent. A method of increasing the solubility of caffeine.

8 Claims, 1 Drawing Sheet

Related U.S. Application Data

(60) Provisional application No. 62/861,718, filed on Jun. 14, 2019.

(51) Int. Cl.

| | |
|---|---|
| ***A23L 2/60*** | (2006.01) |
| ***A23L 33/105*** | (2016.01) |
| ***A23L 33/175*** | (2016.01) |
| ***A61K 9/00*** | (2006.01) |
| ***A61K 9/08*** | (2006.01) |
| ***A61K 31/198*** | (2006.01) |
| ***A61K 36/41*** | (2006.01) |

(56) References Cited

U.S. PATENT DOCUMENTS

| | | | |
|---|---|---|---|
| 2006/0286183 A1 | 12/2006 | Gardiner et al. |
| 2014/0256749 A1 | 9/2014 | Yu |
| 2015/0086654 A1 | 3/2015 | Helmi et al. |
| 2017/0080037 A1 | 3/2017 | Alter |
| 2019/0000126 A1 | 1/2019 | Hesse |
| 2022/0241289 A1 | 8/2022 | Khouider et al. |

FOREIGN PATENT DOCUMENTS

| | | |
|---|---|---|
| WO | 2019038687 A1 | 2/2019 |
| WO | 2020248042 A1 | 12/2020 |

OTHER PUBLICATIONS

Inventor Declaration under 37 CFR §1.132 submitted on Jul. 21, 2025 in U.S. Appl. No. 17/618,557, 1-5. (Year: 2025).*

2019) "Caffeine+ N-Acetyl L-Tyrosine Solution", Natrium Health, 3 pages.

Mar. 19, 2019) "Caffeine+ N-Acetyl L-Tyrosine Solution", Wayback Machine, Nootropics Depot, 5 pages.

2016) "Complementary & Alternative Medicine for Mental Health", Mental Health America, 243 pages.

Corresponding Canadian Patent Application No. 3,143,343 Examination Report, mailed on Apr. 16, 2025, 4 pages.

International Application No. PCT/CA2020/050529 Search Strategy, dated Jul. 21, 2020, 2 pages.

International Search Report and Written Opinion received in PCT Application No. PCT/CA2020/050529, mailed on Jul. 21, 2020, 9 pages.

Jul. 8, 2005) "N-Acetyl-L-Tyrosine", Pubchem, 54 pages.

Jun. 13, 2018) "Solutions", Wayback Machine, Natrium Health, 1 page.

Bock et al. (2004) "Acute Rhodiola Rosea Intake can Improve Endurance Exercise Performance", International Journal of Sport Nutrition and Exercise Metabolism, 14(3):298-307.

Deijen et al. (1994) "Effect of Tyrosine on Cognitive Function and Blood Pressure Under Stress", Brain Research Bulletin, 33(3):319-23.

Deijen et al. (1999) "Tyrosine Improves Cognitive Performance and Reduces Blood Pressure in Cadets after One Week of a Combat Training Course", Brain Research Bulletin, 48(2):203-209.

Duncan et al. (2015) "The Effect of Caffeine and Rhodiola Rosea, Alone or in Combination, on 5-km Running Performance in Men", Journal of Caffeine Research, 6 (1):40-48.

Lee et al. (2013) "Anti-Inflammatory and Neuroprotective Effects of Constituents Isolated from Rhodiola rosea", Evidence Based Complementary and Alternative Medicine, 2013(514049), 9 pages.

Ma et al., "Rhodiola rosea L. Improves Learning and Memory Function: Preclinical Evidence and Possible Mechanisms", Frontiers in Pharmacology, Dec. 2018, 9:1415, 18 pages.

Magill et al. (Aug. 2003) "Effects of Tyrosine, Phentermine, Caffeine D-amphetamine, and Placebo on Cognitive and Motor Performance Deficits During Sleep Deprivation", Nutritional Neuroscience, 6(4):237-246.

Perera et al. (Mar. 2010) "Caffeine and Paraxanthine HPLC Assay for CYP1A2 Phenotype Assessment Using Saliva and Plasma", Biomedical Chromatography, 24(10):1136-1144.

Inventor Declaration under 37 CFR §1.132 submitted on Jul. 21, 2025 in U.S. Appl. No. 17/618,557, 5 pages.

Notice of Allowance issued in U.S. Appl. No. 17/618,557, mailed on Aug. 4, 2025, 8 pages.

* cited by examiner

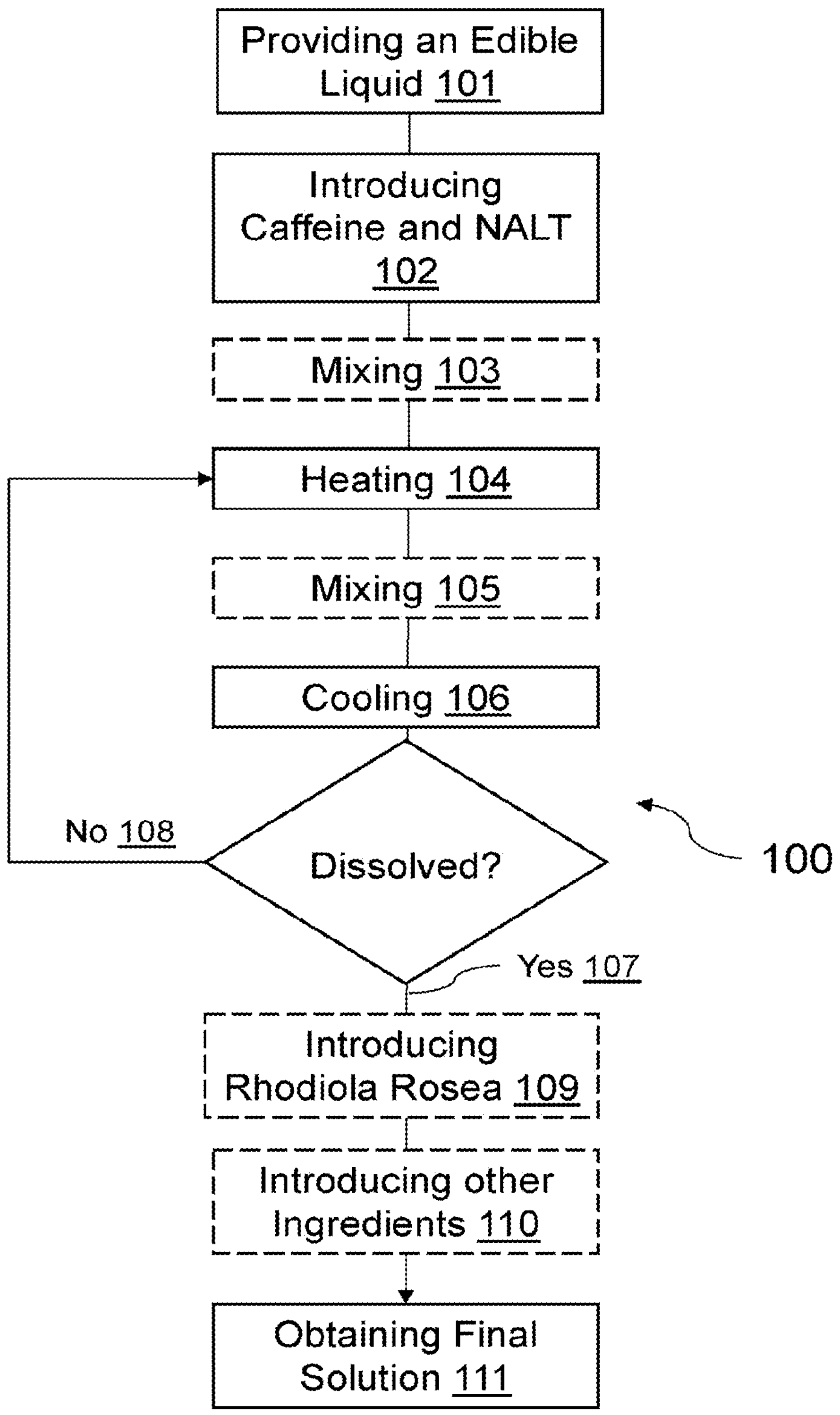
Providing an Edible Liquid 101
Introducing Caffeine and NALT 102
Mixing 103
Heating 104
Mixing 105
Cooling 106
Dissolved?
No 108
Yes 107
Introducing Rhodiola Rosea 109
Introducing other Ingredients 110
Obtaining Final Solution 111
100

STIMULANT COMPOSITION AND PROCESS FOR MAKING SAME

The present patent application is a continuation of U.S. patent application Ser. No. 17/618,557, filed Dec. 13, 2021. U.S. Ser. No. 17/618,557 is a U.S. national stage entry of PCT/CA2020/050529, filed Apr. 22, 2020. PCT/CA2020/050529 claims priority to U.S. provisional patent application No. 62/861,718 filed Jun. 14, 2019. Each of the aforementioned patent applications is hereby incorporated by reference in its entirety.

TECHNICAL FIELD

The present disclosure relates to consumable compositions, and more particularly to consumable compositions with an elevated concentration of caffeine, N-Acetyl-L-Tyrosine (NALT) and/or *Rhodiola rosea.*

BACKGROUND

There are many different stimulants on the market that often use caffeine as the active ingredient, but sometimes include other energy boosting ingredients such as taurine and vitamin-B12. These formulations, which include coffee, energy drinks and energy shots, provide the desired energy boost. However, these formulations almost exclusively come as a single dose due to their relatively low active ingredient concentration. In addition, there have been concerns about their safety profile with regard to the negative effects of caffeine on the body, both over the short term and long term.

Current ways of administering caffeine at a sufficient quantity to provide an energy-boosting effect are often through pill or liquid form. Moreover, a method for providing caffeine in oral-spray form using sodium benzoate to increase the concentration of caffeine is known in the art as outlined in U.S. Pat. No. 5,456,677A. However, the method disclosed in U.S. Pat. No. 5,456,677A is of limited comestible applicability due to sodium benzoate's ability to convert to benzene, a known carcinogen.

Furthermore, despite caffeine achieving a relatively high solubility in boiling water (around 66 g/100 mL of water), this elevated concentration of caffeine is not maintained when the caffeine solution returns to room temperature. In fact, at room temperature, the solubility of caffeine is around 2 g per 100 mL of water. As such, it remains desirable to develop a solution with an elevated concentration of caffeine, where the elevated caffeine concentration remains stable at room temperature. Therefore, it would be advantageous to uncover a method of achieving a highly concentrated caffeine solution (i.e. concentrate) that is suitable for consumption and that is stable at room temperature for easy storage, transport and use.

Additionally, the ingredient *Rhodiola rosea* is generally consumed as a natural health product, usually in tincture, capsule, or pill form in certain amounts. However, these methods of ingestion are not very convenient and provide a delayed onset of the effects.

SUMMARY

The present disclosure relates to formulations with a high concentration of caffeine, and methods of producing same, where the high concentration of caffeine is achieved through the addition of a tyrosine-base compound (e.g. tyrosine or N-Acetyl-L-Tyrosine (NALT)). It has been discovered that tyrosine or NALT, (e.g. in some cases, to accelerate the reaction, preferably when exposed to heat), reacts with caffeine, substantially increasing caffeine's solubility. The concentration of caffeine found in the solution including tyrosine or NALT remains elevated even when the solution returns to room temperature. As such, the unexpected synergy between tyrosine or NALT and caffeine enables the production of a concentrate with highly elevated concentrations of caffeine, going significantly beyond its normal solubility at room temperature, that remains stable at room temperature.

Moreover, the disclosure is directed to a composition, that, in part through the inclusion of other selected active ingredients, mitigates some of caffeine's negative effects on the body.

The composition may also contain a phenylpropanoid selected from the group consisting of rosavin, rosin, rosarin, salidroside, or mixtures thereof (e.g. found in an extract of *Rhodiola rosea* comprising the same—henceforth referred to simply as *Rhodiola rosea*), which is understood to ameliorate the side-effects of caffeine consumption, such as lethargy and reduced cognitive function (i.e. the "caffeine crash") conventionally known to follow caffeine consumption.

In some examples, sweeteners and flavourings may be added to enhance palatability of the solution.

In some embodiments, the composition may also contain vitamins, minerals, emulsifiers and/or preservatives.

A broad aspect of the present disclosure is a composition for use as a stimulant, the composition comprising an ingestible liquid; caffeine; N-Acetyl-L-Tyrosine (NALT); and a phenylpropanoid selected from the group consisting of rosavin, rosin, rosarin, salidroside, or mixtures thereof, or an extract of *Rhodiola rosea* comprising the same.

In some embodiments, the molar ratio of the caffeine and NALT may be about 1:1.

In some embodiments, the ingestible liquid may include water.

In some embodiments, the phenylpropanoid(s) may be contained within *Rhodiola rosea* extract.

In some embodiments, the composition may include one or more sweetener(s).

In some embodiments, the composition may include one or more flavourant(s).

Another broad aspect, in accordance with certain examples, is a process for making a stimulant composition comprising the steps of combining water, caffeine powder and NALT powder in a container; applying a heating-mixing-cooling cycle to the water-caffeine-NALT liquid, the heating-mixing-cooling cycle comprising heating the liquid to boiling; immediately upon the commencement of boiling, removing the liquid from the heat; thoroughly mixing the liquid while it cools to room temperature; and repeating the heating-mixing-cooling cycle until the water-caffeine-NALT liquid becomes transparent and takes on a slight yellowish hue.

In some embodiments, the process may include, after the water-caffeine-NALT liquid becomes transparent and takes on a slight yellowish hue, adding *Rhodiola rosea* extract to the water-caffeine-NALT liquid; applying the heating-mixing-cooling cycle to the water-caffeine-NALT-*Rhodiola rosea* extract liquid; and repeating the heating-mixing-cooling cycle until no particles remain at the bottom of the container.

In some embodiments, the process may include adding Vitamin B12.

In some embodiments, the process may include adding a sweetener.

In some embodiments, the process may include adding a flavourant.

In some embodiments, the process may include adding an emulsifier.

In some embodiments, the process may include adding a preservative.

Another broad aspect is a liquid composition for use as a consumable stimulant.

The composition includes a consumable liquid solvent comprising water; caffeine at a concentration of at least 0.04 g/mL once dissolved in the consumable liquid solvent; and a tyrosine-based compound of the following formula:

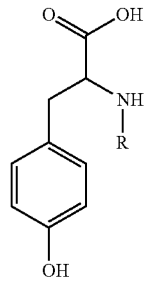

where R is selected from H, an alkyl or acetyl, and wherein a presence of the tyrosine-based compound in the composition results in an increased solubility of the caffeine in the consumable liquid solvent.

In some embodiments, R may be acetyl or hydrogen.

In some embodiments, R may be acetyl, wherein the tyrosine-based compound may be n-acetyl-1-tyrosine.

In some embodiments, the molar ratio of the caffeine and the N-Acetyl-L-Tyrosine in the consumable liquid solvent may be around 1:1.

In some embodiments, the consumable liquid solvent may be water.

In some embodiments, the consumable liquid solvent may be purified water.

In some embodiments, the consumable liquid solvent may include ethanol.

In some embodiments, the concentration of the caffeine may be at least of 0.2 g/mL once dissolved in the consumable liquid solvent, and wherein the concentration of the N-Acetyl-L-Tyrosine may be at least of 0.23 g/mL once dissolved in the consumable liquid solvent.

In some embodiments, the concentration of the caffeine may be at least of 0.4 g/mL once dissolved in the consumable liquid solvent.

In some embodiments, the concentration of the caffeine may range from 0.4 g/mL to 1.488 g/mL once dissolved in the consumable liquid solvent.

In some embodiments, the concentration of the caffeine may range from above 0.02 g/mL to 1.488 g/mL once dissolved in the consumable liquid solvent.

In some embodiments, the composition may include a phenylpropanoid selected from the group consisting of rosavin, rosin, rosarin, salidroside, or a combination thereof.

In some embodiments, the composition may include a sweetener.

In some embodiments, the composition may include a flavourant.

Another broad aspect is a method of increasing the solubility of caffeine in a liquid solution. The method includes introducing an amount of N-Acetyl-L-Tyrosine, or an acceptable salt thereof, and the caffeine, or an acceptable salt thereof, into a liquid solvent comprising water, whereby the presence of the N-Acetyl-L-Tyrosine increases the solubility of the caffeine in the liquid solvent.

In some embodiments, the method may include heating the liquid solution containing the caffeine and the N-Acetyl-L-Tyrosine.

In some embodiments, the method may include the liquid solution is heated to a boil.

In some embodiments, the method may include heating the liquid solvent prior to adding the caffeine and the N-Acetyl-L-Tyrosine.

In some embodiments, the method may include mixing the liquid solution containing the caffeine and the N-Acetyl-L-Tyrosine; and cooling the heated liquid solution containing the caffeine and the N-Acetyl-L-Tyrosine.

In some embodiments, the method may include the cooling includes cooling the heated liquid solution containing the caffeine and the N-Acetyl-L-Tyrosine to room temperature.

In some embodiments, the method may include repeating the heating, mixing and cooling until the caffeine and the N-Acetyl-L-Tyrosine has dissolved.

In some embodiments, the molar ratio of the caffeine and the N-Acetyl-L-Tyrosine added to the consumable liquid solvent may be around 1:1.

Another broad aspect is a consumable liquid caffeine composition with an increased concentration of caffeine obtained by performing the method as defined herein.

In some embodiments, the composition may include a phenylpropanoid selected from the group consisting of rosavin, rosin, rosarin, salidroside, or a combination thereof.

In some embodiments, the phenylpropanoid may be derived from *Rhodiola rosea.*

BRIEF DESCRIPTION OF THE DRAWINGS

The invention will be better understood by way of the following detailed description of embodiments of the invention with reference to the appended drawings, in which:

FIG. 1 is a flowchart diagram of an exemplary process of producing a stimulant composition with an elevated concentration of caffeine.

DETAILED DESCRIPTION

The present disclosure relates to formulations for consumption (e.g. human consumption) that harness the unexpected synergy between a tyrosine-based compound (e.g. tyrosine or N-Acetyl-L-Tyrosine (NALT)) and caffeine in a hydrophilic and consumable solvent (e.g. water, ethanol, water and ethanol mixture, etc.) It has been discovered that the presence of a tyrosine-based compound (e.g. NALT), in a solution containing caffeine (e.g. combined with heating the solution) increases the solubility of caffeine when the solution returns to room temperature. In some embodiments, maintaining a 1:1 molar ratio of caffeine and the tyrosine-based compound results in a further increase in the solubility of caffeine in the mixture, when increasing the concentration of NALT allows for a proportional increase in caffeine in solution. As such, in order to achieve increasingly elevated concentrations of caffeine, it may be necessary to increase proportionally the concentration of NALT in the composition. Similarly, the presence of caffeine in the solution allows for a corresponding increase in the solubility of NALT in the solvent at room temperature.

As such, the synergy between NALT and caffeine may yield a concentrate with such high concentrations of caffeine that may be suitable for ingestion as a spray, where a single dose or spray (e.g. a volume of 0.07 mL to 0.2 mL per spray) may be sufficient to provide the user with a suitable amount of caffeine (e.g. anywhere between 10 to 120 mg of caffeine per spray) and NALT to provide a stimulating effect.

Therefore, it has been discovered that, when combined with caffeine, e.g., through the process outlined below (including, one or more cycles of mixing, heating and cooling), the reaction with NALT increases caffeine's solubility in water (e.g. by approximately 5-fold-may go up to or over 35-fold-35.25 fold), allowing for more compact and efficient energy ingestion, thus accelerating its stimulating effects.

In some embodiments, compositions including *Rhodiola rosea*, Caffeine, and N-Acetyl-L-Tyrosine are provided, which have been demonstrated to work together to increase their collective consumable efficiency and ameliorate conventional adverse effects.

NALT is an acetylated form of tyrosine, which is one of the 20 standard amino acids found in the human body. The compound has been shown to improve mental performance and memory under stressful conditions[1,2], as well as to increase the alertness and mental performance of sleep-deprived individuals[3].

The use of *Rhodiola rosea* with caffeine is understood to mitigate the post-consumption "crash" that is conventionally associated with caffeine[4]. On its own, *Rhodiola rosea* also reduces stress[5], improves endurance[6], acts as a neuroprotectant[7], and improves learning and memory in experimental models[8].

In one embodiment, a composition suitable for the consumption of *Rhodiola rosea* by way of a multi-use portable spray mechanism is provided, in a concentration high enough to be of use (e.g. 3 mg of *Rhodiola rosea* per kg of body weight of the subject). The multiple-use portable oral spray method of delivery provides a convenient and fast-onset transmission of *Rhodiola rosea*'s beneficial effects.

The compositions may also be accompanied by sweeteners, flavourings, vitamins, minerals, and/or other ingredients as desired for taste and other desired specific effects.

Definitions

In the present disclosure, by "container", it is meant an object that is meant to hold something (such as a liquid), and may include, but it not limited to, a bowl, a pot, an Erlenmeyer, a flask, a bottle, a vat, a canister, etc.

In the present disclosure, by "consumable", it is meant something suitable for animal or human consumption.

In the present disclosure, by "flavourant", it is meant a substance that gives another substance flavor. When added to a liquid composition as described herein, the flavourant gives the liquid composition flavour.

In the present disclosure, by "liquid composition", it is meant a liquid solution that is suitable for delivery through ingestion as a liquid, as an aerosol that can be consumed or administered as a spray, through a dropper, as an injection, etc.

In the present disclosure, by "solution" it is meant a homogenous mixture of two or more substances.

In the present disclosure, by "solvent" it is meant the substance in which the solute (e.g. caffeine or acceptable salt, NALT or acceptable salt, etc.) is dissolved.

In the present disclosure, by "stimulant" it is meant a substance that raises the level of physiological or cognitive activity in the body. Stimulants include, but are not limited to, compositions including caffeine, NALT and/or phenylpropanoids such as those found in *Rhodiola rosea* extract.

In the present disclosure, by "tyrosine-based compound", it is meant a compound with the following formula (tyrosine, L-tyrosine, or tyrosine derivative or L-tyrosine derivative):

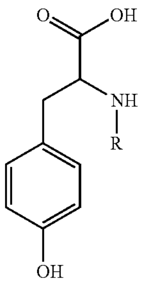

where R is selected from hydrogen, acetyl (resulting in N-Acetyl-L-Tyrosine), alkyl (methyl, ethyl, propyl, isopropyl, butyl, tertbutyl, isobutyl, etc.) etc.

Exemplary Formulations

Reference will now be made in detail to exemplary compositions and methods practicing the teachings described herein, which constitute the best modes of practicing the present teachings presently known to the inventors. The disclosed embodiments are merely exemplary and may be embodied in various forms. Therefore, specific details disclosed herein are not to be interpreted as limiting, but as representative for any aspect of the present teachings.

Except where expressly indicated or in the examples, all quantitative information is to be understood as modified by the word "about" in describing the broadest scope of the invention. Also, unless expressly stated to the contrary: percent, "parts of" and ratio values are by molar ratio, the description of a group or class of materials as suitable or preferred for a given purpose in connection with the invention implies that mixtures of any two or more of the members of the group or class are equally suitable or preferred.

It is to be understood that this invention is not limited to the specific embodiments and methods described below as specific components and/or conditions may vary. The terminology used herein is used only for the purpose of describing particular embodiments of the present invention and is not intended to be limiting in any way.

Throughout this disclosure, where publications are referenced, the disclosures of these publications in their entireties are hereby incorporated by reference into this disclosure to more fully describe the state of the art to which this invention pertains.

The following description of the embodiments is merely exemplary in nature and is in no way intended to limit the invention, its application or uses.

The composition preferably includes caffeine. The regular solubility of caffeine in water at room temperature is of 0.02 g/mL. However, it has been shown that, in the presence of a tyrosine-based compound (e.g. NALT), the solubility of caffeine can be greater than 0.02 g/mL at room temperature. As such, in a refinement, caffeine is present in an amount that is greater than 0.02 g/mL. In a refinement, caffeine is present in an amount that is greater than 0.02 g/ml, up to about 0.1 g/ml. In another refinement, caffeine is present in an amount from about 0.1 g/mL to about 0.4 g/mL. In yet another refinement, caffeine is present from about 0.02 g/ml to 0.4 g/ml. In another refinement, caffeine is present in an amount from about 0.02 g/mL to about 0.587 g/mL. In yet another refinement, caffeine is present from about 0.2 g/ml to 0.587 g/ml.

As such, the composition preferably includes N-Acetyl-L-Tyrosine (NALT) to counteract the side effects of caffeine, and to increase the solubility of caffeine in a hydrophilic solvent. In some embodiments, the concentration of NALT in the solution is sufficient to achieve a 1:1 molar ratio between caffeine and NALT. It has been shown that maintaining a 1:1 molar ratio between caffeine and the tyrosine-based compound (e.g. NALT) further results in an increase in the solubility of caffeine in the hydrophilic solution. In a refinement, NALT is present in an amount from about 0.02 g/ml to 0.2 g/ml. In another refinement, NALT is present from about 0.2 g/ml to 0.4 g/ml.

In some embodiments, the composition may include *Rhodiola rosea* or a derivative thereof. A particularly useful *Rhodiola rosea* derivative is *Rhodiola rosea* extract (containing, for instance, salidrosides and rosavins), which is understood to be a neuroprotective agent. In a refinement, the *Rhodiola rosea* derivative is present in an amount from about 0.09 g/ml to 0.16 g/ml. In another refinement, the *Rhodiola rosea* derivative is present in an amount from about 0.18 g/ml to 0.24 g/ml. In still another refinement, the *Rhodiola rosea* derivative is present in an amount from about 0 g/ml to 0.07 g/ml.

In some embodiments, the composition may include one or more vitamins. One particularly useful example of such vitamins is vitamin B12, as deficiencies of this vitamin have been shown to cause fatigue among other symptoms. In a refinement, vitamins are present in an amount from about 0.0000 g/ml to 0.0001 g/ml. In another refinement, vitamins are present in an amount from about 0.0003 g/ml to 0.0007 g/ml.

In some embodiments, the composition may include the sweetener xylitol for its salivatory properties to counteract caffeine-induced, or otherwise induced, dry mouth. In a refinement, xylitol is present in an amount from about 0.0 g/ml to 0.03 g/ml. In another refinement, xylitol is present in an amount from about 0.05 g/ml to 0.09 g/ml. In a refinement, xylitol is present in an amount from about 0.0 g/ml to 0.09 g/ml. In a refinement, xylitol is present in an amount of 0.04 g/ml. In a refinement, xylitol is present in an amount from about 0.0 g/ml to 0.04 g/ml.

In some embodiments, the composition may contain one or more flavourants and/or additional sweeteners. These are added in order to make the generally unpalatable taste of the other ingredients more appetizing. This is especially pertinent to caffeine as caffeine inherently has a bitter taste. In a refinement of the present disclosure, the flavourant(s) may be present in an amount from about 0.00 g/ml to 0.25 g/ml. In another refinement, the flavourant(s) may be present in an amount from about 0.3 g/ml to 0.6 g/ml. Sucralose is an example of a sweetener that may be used in the present embodiment. In a refinement, the sweetener may be present in an amount from about 0.00 g/ml to 0.15 g/ml. In another refinement, the sweetener may be present in an amount from 0.15 g/ml to 0.30 g/ml.

The flavourants may be common food flavourants. Such food flavourants may include but are not limited to pomegranate flavours, lemon flavours, coffee flavours, chocolate flavours, vanilla flavours, peppermint flavours, spearmint flavours, guava flavours, mango flavours, raspberry flavours, strawberry flavours and the like. The flavourants may be included in a suitable carrier (such as propylene glycol).

The compositions are made by adding selections of the ingredients set forth above into a consumable liquid. Water is a particularly useful liquid for this purpose as it is a natural solvent. Tables 1 through 4 provide exemplary sets of components that may be introduced into such a liquid (with the indicated quantities suitable for a final liquid composition having a total final volume of about 5 ml). However, this size is only for demonstrative purposes and is in no way intended to limit nor advise the container size for the described embodiments. The amounts and combination of ingredients shown in Tables 1-4 are but for illustrative purposes. A skilled person will understand that other amounts and combination of ingredients, including caffeine and NALT, to be introduced into the liquid, may be used without departing from the present teachings.

Tables

TABLE 1

Concentrated Energy Compositions

| Component | Amounts (mg) |
|---|---|
| Caffeine | 1300-1500 |
| *Rhodiola Rosea* Extract | 500-700 |
| Amino Acids | 1300-1500 |
| N-Acetyl-L-Tyrosine | |
| Sweeteners | 150-300 |
| Sucralose | |
| Flavour | 700-900 |
| Flavourants | |
| Vitamins | 0.0-0.1 |
| Vitamin B12 | |
| Preservatives | |
| Sodium Benzoate | 0-75 |
| Potassium Sorbate | 0-75 |

TABLE 2

Concentrated Energy Compositions

| Component | Amounts (mg) |
|---|---|
| Caffeine | 1600-2000 |
| *Rhodiola Rosea* Extract | 300-600 |
| Amino Acids | 1600-2000 |
| N-Acetyl-L-Tyrosine | |
| Sweeteners | 180-400 |
| Sucralose | |
| Flavour | 700-900 |
| Flavourants | |
| Vitamins | 0.0-0.1 |
| Vitamin B12 | |
| Preservatives | |
| Sodium Benzoate | 0-75 |
| Potassium Sorbate | 0-75 |

TABLE 3

Concentrated Energy Compositions

| Component | Amounts (mg) |
|---|---|
| Caffeine | 1300-1500 |
| *Rhodiola Rosea* Extract | 0-400 |
| Amino Acids | 1494-1724 |
| N-Acetyl-L-Tyrosine | |
| Sweeteners | 200-400 |

TABLE 3-continued

| Concentrated Energy Compositions | |
|---|---|
| Component | Amounts (mg) |
| Sucralose | |
| Flavour | 100-300 |
| Flavourants | |
| Vitamins | 0.0-0.1 |
| Vitamin B12 | |
| Preservatives | |
| Sodium Benzoate | 0-75 |
| Potassium Sorbate | 0-75 |

TABLE 4

| Concentrated Energy Compositions | |
|---|---|
| Component | Amounts (mg) |
| Caffeine | 1600-2000 |
| *Rhodiola Rosea* Extract | 300-600 |
| Amino Acids | 1600-2000 |
| N-Acetyl-L-Tyrosine | |
| Sweeteners | 180-400 |
| Sucralose | |
| Flavour | 700-900 |
| Flavourants | |
| Vitamins | 0.0-0.1 |
| Vitamin B12 | |
| Preservatives | |
| Sodium Benzoate | 0-75 |
| Potassium Sorbate | 0-75 |

In an exemplary embodiment, the composition contains:

0.27-0.29 g/ml of caffeine powder (BulkSupplements-.com, Henderson, Nev.);

0.27-0.29 g/ml of NALT (UPC 764442898846, BulkSupplements.com, Henderson, NV);

0.11-0.13 g/ml of *Rhodiola rosea* extract (UPC 849720009524, BulkSupplements.com, Henderson, Nev.);

0.001-0.003 g/ml of 1% Vitamin B12 (Belle Chemical LLC, Billings, Mont.);

a sweetener, e.g., 0.04-0.06 g/ml of sucralose (UPC 849720008961, BulkSupplements.com, Henderson, Nev.); and flavourants (to enhance palatability), being:

0.01-0.02 g/ml of peppermint flavour (ID 0070-0500, LorAnn Oils Inc., Lansing, Mich.);

0.1-0.15 g/ml of coffee flavour (ID 0712-0500, LorAnn Oils Inc., Lansing, Mich.); and 0.01-0.05 g/ml of vanilla flavour (ID 0690-0500, LorAnn Oils Inc., Lansing, Mich.).

It will be understood that in some examples, the ingredients, such as NALT, may be introduced into the liquid as acceptable salts thereof.

Exemplary Compositions of Caffeine and NALT

The following exemplary compositions were achieved to illustrate concentrations of caffeine that can be reached through its combination with a tyrosine-based compound, such as NALT. These are but examples of compositions for the purposes of illustrating the present teachings:

Example 1—587 mg/ml—Heated

Materials:

NALT: 1.642 g=7.356 mmol

Filtered Water: 2.404 g

Caffeine: 1.411 g=7.266 mmol

Procedure:

Ingredients are added, and the solution is stirred. Within 5 secs of stirring, both the caffeine and NALT begin dissolving in the solution. After about 5 mins of stirring, the solution starts to become transparent and takes on a yellowish hue. Only tiny floating white particles are left suspended in the solution. After heating, the solution is warm to the touch, and the particles have become very small as they dissolve in the solution. After 1.5 min of stirring, particles are almost gone. After repeating the above two steps once more, the particles are gone and the solutions is completely transparent with a yellowish hue.

Two days after the procedure, the solution remains transparent with a yellowish-brown hue and has roughly the viscosity of water.

Example 2—1044 mg/ml—Heated

Materials:

NALT: 2.904 g=13.010 mmol

Filtered Water: 2.401 g

Caffeine: 2.506 g=12.905 mmol

Procedure:

Ingredients are added, and the solution is stirred. Within 10 secs of stirring, both the caffeine and NALT begin dissolving and the solution takes on a milky appearance and texture. After 2 mins of stirring the solution, the solution is heated. After heating, the solution is warm to the touch, and the particles have become very small as they dissolve into the solution. After 1.5 min of stirring, the particles become very small, and the solution becomes nearly transparent. After repeating the above two steps three more times and letting the solution sit for 5 mins, the particles are gone and the solution is completely transparent with a yellowish hue.

Two days after the procedure, the solution remains transparent with a yellowish-brown hue and has roughly the viscosity of water.

Example 3—420 mg/ml—Unheated

Materials:

NALT: 1.190 g=5.331 mmol

Filtered Water: 2.400 g

Caffeine: 1.008 g=5.191 mmol

Procedure:

Ingredients are added, then the solution is stirred. Within 10 secs of stirring, both the caffeine and NALT begin dissolving and the solution takes on a milky appearance and texture. After 10 mins of stirring the solution, the solution is transparent.

Two days after the procedure, the solution remains transparent with a yellowish-brown hue and has roughly the viscosity of water.

Example 4—400 mg/ml—Unheated

Materials:

NALT: 1.152 g=5.161 mmol

Filtered Water: 2.400 g

Caffeine: 0.961 g=4.949 mmol

Procedure:

Ingredients are added, and the solution is stirred. Within 10 secs of stirring, both the caffeine and NALT begin dissolving and the solution takes on a milky appearance and texture. After 10 mins of stirring the solution, the solution is transparent.

Two days after the procedure, the solution remains transparent with a yellowish-brown hue and has roughly the viscosity of water.

Example 5—1247 mg/ml—Heated

Materials:
- NALT: 3.485 g=15.612 mmol
- Filtered Water: 2.405 g
- Caffeine: 3.000 g=15.449 mmol Procedure:

Ingredients are added, and the solution is stirred. Within 10 secs of stirring, both the caffeine and NALT begin dissolving and the solution takes on a milky appearance and texture. After 2 mins of stirring the solution, the solution is heated. After heating, the solution is warm to the touch, and the particles have become very small as they dissolve in the solution. After 1.5 min of stirring, the particles become very small, and the solution has become nearly transparent. After repeating the above two steps three more times and letting the solution sit for 15 mins, only a few small particles are left in the solution.

Two days after the procedure, the solution remains transparent with a yellowish-brown hue and has roughly the viscosity of water.

Example 6—1,488 mg/ml—Heated

Materials:
- NALT: 4.165 g=18.659 mmol
- Filtered Water: 2.420 g
- Caffeine: 3.601 g=18.544 mmol Procedure:

Ingredients are added, and the solution is stirred. At first the solution is like a thick paste, but it quickly becomes much less viscous. Within 10 secs of stirring, the solution gains a milky appearance and texture. After 2 mins of stirring the solution, the solution begins to take on a yellowish hue, and the solution is heated. After heating, the solution is warm to the touch, and the solution has become much less viscous. After 1.5 min of stirring, the solution is heated again. After 1.5 min of stirring the solution is heated again until the solution begins to boil. After letting the solution sit for 15 mins, the small bubbles that were trapped in the solution are gone, but tiny white particles remain suspended. After repeating the above two steps once again, the solution is mostly transparent.

Two days after the procedure, the solution is transparent with a yellowish-brown hue, however the viscosity has increased and is greater than that of water.

Example 7—475 mg/ml—Unheated

Materials:
- NALT: 1.341 g=6.008 mmol
- Filtered Water: 2.404 g
- Caffeine: 1.142 g=5.881 mmol Procedure:

Ingredients are added, and the solution is stirred. Within 10 secs of stirring, both the caffeine and NALT begin dissolving and the solution takes on a milky appearance and texture. After 10 mins of stirring, the solution is transparent with a yellowish hue.

Even though the examples provided herein refer to NALT, it has been discovered that the phenol group of NALT may be involved at least in intermolecular bonding that may increase the solubility of caffeine in solution. Moreover, the carboxyl group of L-Tyrosine or NALT may also play a role in increasing solubility. As such, it is possible that tyrosine and other tyrosine-derivatives (e.g. where the carboxyl group remains unsubstituted) may also increase, like NALT, the solubility of caffeine when present with caffeine in solution.

Exemplary Process of Producing a Solution with an Elevated Concentration of Caffeine Reference will now be made to FIG. 1, illustrating an exemplary process 100 for producing a solution with an elevated concentration of caffeine as disclosed herein.

A volume of consumable liquid solvent (e.g. water, such as a purified water) is provided at step 101.

A tyrosine-based compound (N-Acetyl-L-Tyrosine will be used herein for purposes of illustration) and caffeine powders (or acceptable salts thereof) are added to the liquid solvent at step 102. In preferred embodiments, equal molar amounts of NALT and caffeine may be added to the liquid solvent.

The composition may be preferably mixed in order to promote the reaction of the two ingredients at step 103.

In preferred embodiments, the mixture is heated (e.g. preferably brought to a boil) at step 104. In some embodiments, the liquid may be heated prior to adding the NALT and caffeine powders. Heating is shown to increase the amount of caffeine that can be dissolved with NALT. As shown in the examples presented herein, in the presence of NALT, elevated amounts of caffeine (when compared to the solubility of caffeine at room temperature) remain dissolved in the solvent even when the solution returns to room temperature (caffeine does not precipitate at certain concentrations above the normal solubility of caffeine at room temperature).

In preferred embodiments, the mixture is mixed at step 105 (e.g. after being taken off the heat).

In preferred embodiments, the mixture is then cooled (e.g. preferably cooled down to room temperature) at step 106. The combination of NALT and caffeine results in an increase in solubility of caffeine and NALT when compared to a solution where only one component is present.

If NALT and/or caffeine are not yet dissolved at 107, steps 104-106 may be repeated any number of times (e.g. 2-5 times) until the powders are dissolved in the liquid solvent. 2-5 heating and cooling cycles may be generally sufficient, but the number of cycles is dependent on the quantity of ingredients being reacted. It is understood that the two compounds are completely reacted and dissolved when the solution becomes completely transparent (e.g. may take on a slight yellowish hue), where the viscosity may be similar to that of water.

In some embodiments, NALT and caffeine may be added in gradual batches, where steps 102-106 may be repeated per addition of NALT and caffeine. Steps 104-106 may be repeated per each addition of NALT and caffeine until the powders have dissolved.

If the NALT and caffeine powders are dissolved at 108, *Rhodiola* rosea powder and/or isolated phenylpropanoids may then be cut in (introduced into) and dissolved in the solution at step 109. The heating and cooling steps 104-106 (e.g. 2-5 cycles, yet number of cycles may depend on the amount of *Rhodiola rosea* powder introduced into the solution) may be repeated to dissolve the *Rhodiola rosea* powder, which may lead to a dark brownish colour.

Other ingredients, such as sweeteners, vitamins, flavourants or any additional ingredients, can be introduced and dissolved in the liquid solvent at step 110 by, e.g., introducing these ingredients at any time into the solution (e.g. through mixing), thereby obtaining the final solution 111. In some embodiments, it may be preferable to introduce flavourants last as they are often alcohol-based, and the heating processes can evaporate their solvents.

An exemplary process for producing an exemplary volume of about 5 mL of an embodiment of the composition may involve the steps of:

putting 2.6 mL of purified or distilled water in a container suitable for use in heating the water to boiling (e.g., a glass container);
adding 0.01 g of 1% Vitamin B12 and 0.25 g of sucralose to the water;
mixing the liquid until the Vitamin B12 and sucralose are fully dissolved;
adding 1.4 g of caffeine powder to the liquid;
briefly mixing the liquid;
adding 1.4 g of NALT powder;
mixing the liquid for 1 minute;
applying a heating-mixing-cooling cycle, involving:
heating the liquid to boiling;
immediately upon the commencement of boiling, removing the liquid from the heat;
thoroughly mixing the liquid while it cools down to room temperature;
repeating the heating-mixing-cooling cycle until the liquid becomes completely transparent and takes on a slight yellowish hue (indicating that the caffeine and NALT have fully reacted and dissolved);
adding 0.6 g of *Rhodiola rosea* extract;
thoroughly mixing the liquid for 1 minute;
repeating the heating-mixing-cooling cycle until no particles remain at the bottom of the container (indicating that the *Rhodiola rosea* extract is fully dissolved);
adding 0.6 g of coffee flavour, 0.05 g of peppermint flavour, and 0.15 g of vanilla flavour to the liquid; and
thoroughly mixing the liquid until it has a uniform appearance (generally about 1 minute).

Although the invention has been described with reference to preferred embodiments, it is to be understood that modifications may be resorted to as will be apparent to those skilled in the art. Such modifications and variations are to be considered within the purview and scope of the present invention.

Representative, non-limiting examples of the present invention were described above in detail with reference to the attached drawing. This detailed description is merely intended to teach a person of skill in the art further details for practicing preferred aspects of the present teachings and is not intended to limit the scope of the invention. Furthermore, each of the additional features and teachings disclosed above and below may be utilized separately or in conjunction with other features and teachings.

Moreover, combinations of features and steps disclosed in the above detailed description, as well as in the experimental examples, may not be necessary to practice the invention in the broadest sense, and are instead taught merely to particularly describe representative examples of the invention. Furthermore, various features of the above-described representative examples, as well as the various independent and dependent claims below, may be combined in ways that are not specifically and explicitly enumerated in order to provide additional useful embodiments of the present teachings.

CITATIONS

1. Deijen, J. B., Wientjes, C. J. E., Vullinghs, H. F. M., Cloin, P. A. & Langefeld, J. J. Tyrosine improves cognitive performance and reduces blood pressure in cadets after one week of a combat training course. Brain Research Bulletin 48, (1999).
2. Deijen, J. B. & Orlebeke, J. F. Effect of tyrosine on cognitive function and blood pressure under stress. Brain Research Bulletin 33, (1994).
3. Magill, R. A. et al. Effects of Tyrosine, Phentermine, Caffeine d-amphetamine, and Placebo on Cognitive and Motor Performance Deficits During Sleep Deprivation. Nutritional Neuroscience 6, (2003).
4. Duncan, M. J., Tallis, J., Wilson, S. & Clarke, N. D. The Effect of Caffeine and *Rhodiola rosea*, Alone or in Combination, on 5-km Running Performance in Men. Journal of Caffeine Research 6, (2015).
5. Mental Health America. Complementary & Alternative Medicine for Mental Health. (2016).
6. Bock, K. de, Eijnde, B. O., Ramaekers, M. & Hespel, P. Acute *Rhodiola rosea* Intake Can Improve Endurance Exercise Performance. (2004).
7. Lee, Y. et al. Anti-Inflammatory and Neuroprotective Effects of Constituents Isolated from *Rhodiola rosea*. Evidence-based complementary and alternative medicine: eCAM 2013, (2013).
8. Ma, G. et al. *Rhodiola rosea* L. Improves Learning and Memory Function: Preclinical Evidence and Possible Mechanisms. 9, (2018).

What is claimed is:

1. A method for providing caffeine to a subject in need, the method comprising orally administering to the subject a caffeine and N-Acetyl-L-Tyrosine-based solution as a spray, wherein the solution comprises a caffeine concentration of 0.1 g/mL to 1.488 g/mL and a molar ratio of the N-Acetyl-L-Tyrosine and the caffeine that is about 1:1; wherein oral administration of the solution as a spray provides fast-onset transmission of the caffeine's stimulating effects to the subject in need.

2. The method of claim 1, wherein the solution comprises water.

3. The method of claim 1, wherein the solution further comprises one or more of Vitamin B12, a sweetener, a flavourant, an emulsifier, and a preservative.

4. The method of claim 1, wherein the solution further comprises a phenylpropanoid selected from the group consisting of rosavin, rosin, rosarin, and salidroside, or a combination thereof.

5. The method of claim 4, wherein the phenylpropanoid is derived from *Rhodiola rosea*.

6. The method of claim 1, wherein the concentration of the caffeine is at least 0.2 g/mL.

7. The method of claim 1, wherein the concentration of the caffeine is at least 0.4 g/mL.

8. A spray bottle comprising:
a multi-use portable spray mechanism;
a container; and
a food supplement held within said container, wherein the food supplement comprises caffeine at a concentration of 0.1 g/mL to 1.488 g/mL and an amount of N-Acetyl- L-Tyrosine such that a molar ratio of the N-Acetyl-L-Tyrosine and the caffeine is about 1:1.

* * * * *